(12) United States Patent
Torrie

(10) Patent No.: US 10,682,133 B2
(45) Date of Patent: Jun. 16, 2020

(54) SUTURE PASSER AND GRASPER INSTRUMENT AND METHOD

(71) Applicant: Smith & Nephew, Inc., Memphis, TN (US)

(72) Inventor: Paul Alexander Torrie, Marblehead, MA (US)

(73) Assignee: Smith & Nephew, Inc., Memphis, TN (US)

(*) Notice: Subject to any disclaimer, the term of this patent is extended or adjusted under 35 U.S.C. 154(b) by 324 days.

(21) Appl. No.: 15/794,509

(22) Filed: Oct. 26, 2017

(65) Prior Publication Data

US 2018/0116652 A1   May 3, 2018

Related U.S. Application Data

(60) Provisional application No. 62/414,886, filed on Oct. 31, 2016.

(51) Int. Cl.
| | | |
|---|---|---|
| *A61B 17/04* | (2006.01) | |
| *A61B 17/06* | (2006.01) | |
| *A61B 17/00* | (2006.01) | |
| *A61B 90/00* | (2016.01) | |

(52) U.S. Cl.
CPC ...... *A61B 17/0469* (2013.01); *A61B 17/0482* (2013.01); *A61B 17/0483* (2013.01); *A61B 17/0485* (2013.01); *A61B 17/06109* (2013.01); *A61B 2017/00349* (2013.01); *A61B 2017/00367* (2013.01); *A61B 2017/00477* (2013.01); *A61B 2017/061* (2013.01); *A61B 2017/06009* (2013.01); *A61B 2090/034* (2016.02)

(58) Field of Classification Search
CPC ............ A61B 17/0469; A61B 17/0482; A61B 17/0483; A61B 17/0485; A61B 2017/00349; A61B 2017/06009; A61B 17/06109; A61B 2017/00367; A61B 2017/00477; A61B 2017/061; A61B 2090/034
See application file for complete search history.

(56) References Cited

U.S. PATENT DOCUMENTS

| | | |
|---|---|---|
| 17,272 A | 5/1857 | Garvey |
| 349,791 A | 9/1886 | Gibboney, Jr. |
| 373,372 A | 11/1887 | King |
| 421,919 A | 2/1890 | Fergen |
| 424,518 A | 4/1890 | Van Norman |
| 472,440 A | 4/1892 | McVay et al. |
| 652,175 A | 6/1900 | Felson |

(Continued)

FOREIGN PATENT DOCUMENTS

| | | |
|---|---|---|
| EP | 0136262 A2 | 4/1985 |
| EP | 207545 | 1/1987 |

(Continued)

OTHER PUBLICATIONS

International Search Report and Written Opinion in corresponding PCT application No. PCT/US2017/058460, dated Feb. 12, 2018.

*Primary Examiner* — Gregory A Anderson
(74) *Attorney, Agent, or Firm* — Burns & Levinson, LLP; Joseph M. Maraia

(57) ABSTRACT

Disclosed herein is a combination suture passer and grasper instrument having a needle which can deliver a suture to a repair site, and then use deformable wire arms to capture the suture and drag it into a hollow interior of the needle, thus eliminating the need for two separate instruments.

31 Claims, 6 Drawing Sheets

(56) References Cited

U.S. PATENT DOCUMENTS

| | | |
|---|---|---|
| 659,422 A | 10/1900 | Shidler |
| 671,337 A | 4/1901 | Gibson |
| 786,000 A | 3/1905 | Botkin |
| 854,147 A | 5/1907 | Carillon |
| 919,138 A | 4/1909 | Drake et al. |
| 1,009,065 A | 11/1911 | Hanh et al. |
| 1,037,864 A | 9/1912 | Carlson |
| 1,066,317 A | 7/1913 | Pirnat |
| 1,293,565 A | 2/1919 | Smit |
| 1,449,087 A | 3/1923 | Bugbee |
| 1,464,832 A | 8/1923 | Richardson |
| 1,579,379 A | 4/1926 | Marbel |
| 1,635,066 A | 7/1927 | Wells |
| 1,641,077 A | 8/1927 | Fouquet |
| 1,656,467 A | 1/1928 | Ammen |
| 1,815,725 A | 7/1931 | Pilling |
| 1,822,330 A | 9/1931 | Ainslie |
| 1,855,546 A | 4/1932 | File |
| 1,856,721 A | 5/1932 | Nagelmann |
| 1,876,792 A | 9/1932 | Thompson |
| 1,933,024 A | 10/1933 | Nagelmann |
| 2,023,807 A | 12/1935 | Gruss |
| 2,042,403 A | 5/1936 | Hrivnak |
| 2,065,659 A | 12/1936 | Cullen |
| 2,212,830 A | 8/1940 | Anastasi |
| 2,316,297 A | 4/1943 | Southerland |
| 2,348,218 A | 5/1944 | Karle |
| 2,396,180 A | 3/1946 | Karle |
| 2,411,118 A | 11/1946 | Schuster |
| 2,414,746 A | 1/1947 | Karle |
| 2,414,882 A | 1/1947 | Longfellow |
| 2,434,133 A | 1/1948 | Volk |
| 2,577,240 A | 12/1951 | Findley |
| 2,579,192 A | 12/1951 | Kohl |
| 2,593,622 A | 4/1952 | Stanelle |
| 2,601,564 A | 6/1952 | Smith |
| 2,610,631 A | 9/1952 | Calicchio |
| 2,611,366 A | 9/1952 | Mull |
| 2,646,045 A | 7/1953 | Priestley |
| 2,738,790 A | 3/1956 | Todt et al. |
| 2,808,055 A | 10/1957 | Thayer |
| 2,880,728 A | 4/1959 | Rights |
| 2,895,478 A | 7/1959 | Post |
| 2,959,172 A | 11/1960 | Held |
| 3,013,559 A | 12/1961 | Thomas |
| 3,036,482 A | 5/1962 | Kenworthy |
| 3,073,311 A | 1/1963 | Tibbs et al. |
| 3,090,386 A | 5/1963 | Curtis |
| 3,139,089 A | 6/1964 | Schwerin |
| 3,349,772 A | 10/1967 | Rygg |
| 3,372,477 A | 3/1968 | Hoppe |
| 3,393,687 A | 7/1968 | Whitman |
| 3,417,752 A | 12/1968 | Butler |
| 3,470,834 A | 10/1969 | Bone |
| 3,470,875 A | 10/1969 | Johnson |
| 3,638,653 A | 2/1972 | Berry |
| 3,687,138 A | 8/1972 | Jarvik |
| 3,716,058 A | 2/1973 | Tanner |
| 3,752,516 A | 8/1973 | Mumma |
| 3,763,860 A | 10/1973 | Clarke |
| 3,807,407 A | 4/1974 | Schweizer |
| 3,840,017 A | 10/1974 | Violante |
| 3,842,824 A | 10/1974 | Neufeld |
| 3,842,840 A | 10/1974 | Schweizer |
| 3,856,018 A | 12/1974 | Perisse |
| 3,871,379 A | 3/1975 | Clarke |
| 3,890,975 A | 6/1975 | McGregor |
| 3,901,244 A | 8/1975 | Schweizer |
| 3,946,740 A | 3/1976 | Bassett |
| 3,980,177 A | 9/1976 | McGregor |
| 3,985,138 A | 10/1976 | Jarvik |
| 3,990,619 A | 11/1976 | Russell |
| 4,027,608 A | 6/1977 | Arbuckle |
| 4,064,881 A | 12/1977 | Meredith |
| 4,109,658 A | 8/1978 | Hughes |
| 4,161,951 A | 7/1979 | Scanlan, Jr. |
| 4,164,225 A | 8/1979 | Johnson et al. |
| 4,169,476 A | 10/1979 | Hiltebrandt |
| 4,224,947 A | 9/1980 | Fukuda |
| 4,235,238 A | 11/1980 | Ogiu |
| 4,236,470 A | 12/1980 | Stenson |
| 4,312,337 A | 1/1982 | Donohue |
| 4,326,531 A | 4/1982 | Shimonaka |
| 4,345,600 A | 8/1982 | Rothfuss |
| 4,345,601 A | 8/1982 | Fukuda |
| 4,373,530 A | 2/1983 | Kilejian |
| 4,384,406 A | 5/1983 | Tischlinger |
| 4,414,466 A | 11/1983 | Fischer et al. |
| 4,414,908 A | 11/1983 | Yasukata |
| 4,423,729 A | 1/1984 | Gray |
| 4,440,171 A | 4/1984 | Nomoto et al. |
| 4,441,497 A | 4/1984 | Paudler |
| 4,448,194 A | 5/1984 | DiGiovanni et al. |
| 4,463,753 A | 8/1984 | Gustilo |
| 4,471,781 A | 9/1984 | Di Giovanni et al. |
| 4,493,323 A | 1/1985 | Albright |
| 4,500,024 A | 2/1985 | DiGiovanni et al. |
| 4,509,516 A | 4/1985 | Richmond |
| 4,512,344 A | 4/1985 | Barber |
| 4,535,768 A | 8/1985 | Hourahane |
| 4,539,474 A | 9/1985 | Li |
| 4,553,543 A | 11/1985 | Amarasinghe |
| 4,553,544 A | 11/1985 | Nomoto et al. |
| 4,557,265 A | 12/1985 | Andersson |
| 4,574,805 A | 3/1986 | Lerner |
| 4,580,563 A | 4/1986 | Gross |
| 4,590,929 A | 5/1986 | Klein |
| 4,596,249 A | 6/1986 | Freda et al. |
| 4,602,635 A | 7/1986 | Mulhollan et al. |
| 4,621,639 A | 11/1986 | Transue et al. |
| 4,621,640 A | 11/1986 | Mulhollan et al. |
| 4,633,869 A | 1/1987 | Schmieding |
| 4,636,121 A | 1/1987 | Miller |
| 4,641,652 A | 2/1987 | Hutter et al. |
| 4,643,178 A | 2/1987 | Nastari |
| 4,660,559 A | 4/1987 | McGregor |
| 4,662,068 A | 5/1987 | Polonsky |
| 4,712,545 A | 12/1987 | Honkanen |
| 4,716,893 A | 1/1988 | Fischer et al. |
| 4,723,546 A | 2/1988 | Zagorski |
| 4,739,751 A | 4/1988 | Sapega et al. |
| 4,741,330 A | 5/1988 | Hayhurst |
| 4,778,468 A | 10/1988 | Hunt |
| 4,779,616 A | 10/1988 | Johnson |
| 4,781,190 A | 11/1988 | Lee |
| 4,787,377 A | 11/1988 | Laboureau |
| 4,790,312 A | 12/1988 | Capuano et al. |
| 4,836,205 A | 6/1989 | Barrett |
| 4,846,799 A | 7/1989 | Tanaka et al. |
| 4,870,957 A | 10/1989 | Globe et al. |
| 4,871,289 A | 10/1989 | Choiniere |
| 4,881,537 A | 11/1989 | Henning |
| 4,884,572 A | 12/1989 | Bays |
| 4,890,615 A | 1/1990 | Caspari |
| 4,895,148 A | 1/1990 | Bays |
| 4,899,743 A | 2/1990 | Nicholson |
| 4,915,107 A | 4/1990 | Rebuffat |
| 4,923,461 A | 5/1990 | Caspari |
| 4,926,860 A | 5/1990 | Stice |
| 4,932,961 A | 6/1990 | Wong et al. |
| 4,935,027 A | 6/1990 | Yoon |
| 4,950,285 A | 8/1990 | Wilk |
| 4,955,897 A | 9/1990 | Ship |
| 4,957,498 A | 9/1990 | Caspari |
| 4,961,741 A | 10/1990 | Hayhurst |
| 4,976,715 A | 12/1990 | Bays |
| 5,002,563 A | 3/1991 | Pyka et al. |
| 5,013,292 A | 5/1991 | Lemay |
| 5,015,250 A | 5/1991 | Foster |
| 5,037,422 A | 8/1991 | Hayhurst |
| 5,037,433 A | 8/1991 | Wilk |
| 5,053,047 A | 10/1991 | Yoon |
| 5,056,350 A | 10/1991 | Williams |
| 5,059,201 A | 10/1991 | Asnis |

(56) References Cited

U.S. PATENT DOCUMENTS

| | | |
|---|---|---|
| 5,084,058 A | 1/1992 | Li |
| 5,085,661 A | 2/1992 | Moss |
| 5,087,263 A | 2/1992 | Li |
| 5,100,415 A | 3/1992 | Hayhurst |
| 5,100,418 A | 3/1992 | Yoon |
| 5,100,421 A | 3/1992 | Christoudias |
| 5,120,318 A | 6/1992 | Nallapareddy |
| 5,123,913 A | 6/1992 | Wilk |
| 5,129,912 A | 7/1992 | Noda |
| 5,133,723 A | 7/1992 | Li et al. |
| 5,149,329 A | 9/1992 | Richardson |
| 5,152,764 A | 10/1992 | Goble |
| 5,152,769 A | 10/1992 | Baber |
| 5,152,790 A | 10/1992 | Rosenberg et al. |
| 5,163,946 A | 11/1992 | Li |
| 5,174,087 A | 12/1992 | Bruno |
| 5,176,691 A | 1/1993 | Pierce |
| 5,178,629 A | 1/1993 | Kammerer |
| 5,181,919 A | 1/1993 | Bergman et al. |
| 5,188,636 A | 2/1993 | Fedotov |
| 5,192,287 A | 3/1993 | Fournier |
| 5,201,741 A | 4/1993 | Dulebohn |
| 5,201,743 A | 4/1993 | Haber et al. |
| 5,201,744 A | 4/1993 | Jones |
| 5,211,650 A | 5/1993 | Noda |
| 5,217,471 A | 6/1993 | Burkhart |
| 5,217,486 A | 6/1993 | Rice et al. |
| 5,219,358 A | 6/1993 | Bendel |
| 5,222,508 A | 6/1993 | Contarini |
| 5,222,962 A | 6/1993 | Burkhart |
| 5,222,976 A | 6/1993 | Yoon |
| 5,222,977 A | 6/1993 | Esser |
| 5,224,955 A | 7/1993 | West |
| 5,234,443 A | 8/1993 | Phan et al. |
| 5,234,444 A | 8/1993 | Christoudias |
| 5,242,458 A | 9/1993 | Bendel et al. |
| 5,248,231 A | 9/1993 | Denham et al. |
| 5,250,054 A | 10/1993 | Li |
| 5,250,055 A | 10/1993 | Moore et al. |
| 5,254,126 A | 10/1993 | Filipe et al. |
| 5,257,637 A | 11/1993 | El Gazayerli |
| 5,259,846 A | 11/1993 | Granger et al. |
| 5,261,917 A | 11/1993 | Hasson |
| 5,266,075 A | 11/1993 | Clark |
| 5,269,783 A | 12/1993 | Sander |
| 5,269,786 A | 12/1993 | Morgan |
| 5,269,791 A | 12/1993 | Mayzels |
| 5,273,024 A | 12/1993 | Menon |
| 5,275,613 A | 1/1994 | Haber et al. |
| 5,281,234 A | 1/1994 | Wilk |
| 5,282,809 A | 2/1994 | Kammerer et al. |
| 5,292,327 A | 3/1994 | Dodd et al. |
| 5,304,184 A | 4/1994 | Hathaway |
| 5,304,185 A | 4/1994 | Taylor |
| 5,306,280 A | 4/1994 | Bregan et al. |
| 5,308,353 A | 5/1994 | Beurrier |
| 5,312,422 A | 5/1994 | Trott |
| 5,318,577 A | 6/1994 | Li |
| 5,318,579 A | 6/1994 | Chow |
| 5,320,632 A | 6/1994 | Heidmueller |
| 5,327,896 A | 7/1994 | Schmieding |
| 5,334,198 A | 8/1994 | Hart et al. |
| 5,336,239 A | 8/1994 | Gimpelson |
| 5,356,419 A | 10/1994 | Chow |
| 5,364,408 A | 11/1994 | Gordon |
| 5,364,409 A | 11/1994 | Kuwabara |
| 5,368,601 A | 11/1994 | Beurrier et al. |
| 5,368,606 A | 11/1994 | Marlow et al. |
| 5,372,604 A | 12/1994 | Trott |
| 5,374,275 A | 12/1994 | Bradley |
| 5,376,096 A | 12/1994 | Foster |
| 5,382,257 A | 1/1995 | Lewis |
| 5,387,221 A | 2/1995 | Bisgaard |
| 5,387,227 A | 2/1995 | Grice |
| 5,389,103 A | 2/1995 | Heidmueller |
| 5,391,170 A | 2/1995 | McGuire et al. |
| 5,391,173 A | 2/1995 | Wilk |
| 5,393,302 A | 2/1995 | Clark et al. |
| 5,397,325 A | 3/1995 | Della Badia et al. |
| 5,403,328 A | 4/1995 | Shallman |
| 5,403,329 A | 4/1995 | Hinchcliffe |
| 5,409,494 A | 4/1995 | Morgan |
| 5,417,699 A | 5/1995 | Klein et al. |
| 5,417,701 A | 5/1995 | Holmes |
| 5,423,837 A | 6/1995 | Mericle |
| 5,425,733 A | 6/1995 | Schmieding |
| 5,431,678 A | 7/1995 | Rogers |
| 5,433,722 A | 7/1995 | Sharpe |
| 5,439,467 A | 8/1995 | Legome |
| 5,441,502 A | 8/1995 | Bartlett |
| 5,441,507 A | 8/1995 | Wilk |
| 5,443,509 A | 8/1995 | Boucher et al. |
| 5,449,367 A | 9/1995 | Kadry |
| 5,454,823 A | 10/1995 | Richardson |
| 5,456,246 A | 10/1995 | Schmieding |
| 5,462,562 A | 10/1995 | Elkus |
| 5,464,425 A | 11/1995 | Skiba |
| 5,466,243 A | 11/1995 | Schmieding |
| 5,470,338 A | 11/1995 | Whitfield |
| 5,474,565 A | 12/1995 | Trott |
| 5,478,344 A | 12/1995 | Nicholas |
| 5,478,345 A | 12/1995 | Farascioni |
| 5,480,406 A | 1/1996 | Nolan et al. |
| 5,496,331 A | 3/1996 | Xu |
| 5,496,335 A | 3/1996 | Thomason |
| 5,499,991 A | 3/1996 | Garman |
| 5,501,688 A | 3/1996 | Whiteside |
| 5,501,692 A | 3/1996 | Riza |
| D368,776 S | 4/1996 | Toy et al. |
| 5,505,735 A | 4/1996 | Li |
| 5,507,755 A | 4/1996 | Chin |
| 5,507,757 A | 4/1996 | Sauer et al. |
| 5,520,696 A | 5/1996 | Wenstrom, Jr. |
| 5,520,703 A | 5/1996 | Essig et al. |
| 5,522,820 A | 6/1996 | Caspari et al. |
| 5,527,321 A | 6/1996 | Hinchliffe |
| 5,527,322 A | 6/1996 | Klien et al. |
| 5,540,705 A | 7/1996 | Meade |
| 5,545,170 A | 8/1996 | Hart |
| 5,549,613 A | 8/1996 | Goble et al. |
| 5,549,618 A | 8/1996 | Fleenor |
| 5,549,636 A | 8/1996 | Li |
| 5,554,171 A | 9/1996 | Gatturna et al. |
| 5,562,683 A | 10/1996 | Chan |
| 5,562,686 A | 10/1996 | Sauer |
| 5,562,687 A | 10/1996 | Chan |
| 5,562,696 A | 10/1996 | Nobles et al. |
| 5,565,122 A | 10/1996 | Zinnbauer et al. |
| 5,569,269 A | 10/1996 | Hart |
| 5,569,299 A | 10/1996 | Dill |
| 5,569,301 A | 10/1996 | Granger et al. |
| 5,571,090 A | 11/1996 | Sherts |
| 5,573,008 A | 11/1996 | Robinson |
| 5,573,542 A | 11/1996 | Stevens |
| 5,573,543 A | 11/1996 | Stevens |
| 5,575,801 A | 11/1996 | Habermeyer et al. |
| 5,578,044 A | 11/1996 | Cooper |
| 5,584,835 A | 12/1996 | Greenfield |
| 5,586,986 A | 12/1996 | Hinchliffe |
| 5,591,179 A | 1/1997 | Edelstein |
| 5,591,180 A | 1/1997 | Hinchliffe |
| 5,601,557 A | 2/1997 | Hayhurst |
| 5,601,571 A | 2/1997 | Moss |
| 5,603,718 A | 2/1997 | Xu |
| 5,607,435 A | 3/1997 | Sachdeva |
| 5,618,290 A | 4/1997 | Smoot, Jr. |
| 5,618,304 A | 4/1997 | Hart et al. |
| 5,626,588 A | 5/1997 | Sauer et al. |
| 5,626,590 A | 5/1997 | Wilk |
| 5,630,825 A | 5/1997 | De La Torre |
| 5,632,748 A | 5/1997 | Beck, Jr. et al. |
| 5,632,751 A | 5/1997 | Piraka |
| 5,643,266 A | 7/1997 | Li |
| 5,643,289 A | 7/1997 | Sauer et al. |

(56) References Cited

U.S. PATENT DOCUMENTS

| | | |
|---|---|---|
| 5,643,292 A | 7/1997 | Hart |
| 5,645,552 A | 7/1997 | Sherts |
| 5,649,939 A | 7/1997 | Reddick |
| 5,653,716 A | 8/1997 | Malo et al. |
| 5,658,289 A | 8/1997 | Boucher et al. |
| 5,658,299 A | 8/1997 | Hart |
| 5,662,658 A | 9/1997 | Wenstrom, Jr. |
| 5,662,665 A | 9/1997 | Ludwick |
| 5,665,096 A | 9/1997 | Yoon |
| 5,667,526 A | 9/1997 | Levin |
| 5,674,229 A | 10/1997 | Tovey et al. |
| 5,674,230 A | 10/1997 | Tovey et al. |
| 5,681,333 A | 10/1997 | Burkhart |
| 5,690,652 A | 11/1997 | Wurster et al. |
| 5,690,653 A | 11/1997 | Richardson |
| 5,690,677 A | 11/1997 | Schmieding et al. |
| 5,693,061 A | 12/1997 | Pierce et al. |
| 5,693,071 A | 12/1997 | Gorecki et al. |
| 5,695,522 A | 12/1997 | LeMaire et al. |
| 5,697,950 A | 12/1997 | Fucci et al. |
| 5,700,023 A | 12/1997 | Bueina et al. |
| 5,700,273 A | 12/1997 | Buelna et al. |
| 5,707,379 A | 1/1998 | Fleenor et al. |
| 5,709,694 A | 1/1998 | Greenberg et al. |
| 5,713,908 A | 2/1998 | Jameel et al. |
| 5,728,107 A | 3/1998 | Zlock et al. |
| 5,728,112 A | 3/1998 | Yoon |
| 5,728,113 A | 3/1998 | Sherts |
| 5,728,135 A | 3/1998 | Bregen |
| 5,730,747 A | 3/1998 | Ek et al. |
| 5,735,862 A | 4/1998 | Jennings et al. |
| 5,741,278 A | 4/1998 | Stevens |
| 5,746,751 A | 5/1998 | Sherts |
| 5,746,753 A | 5/1998 | Sullivan |
| 5,749,879 A | 5/1998 | Middleman et al. |
| 5,752,964 A | 5/1998 | Mericle |
| 5,755,728 A | 5/1998 | Maki |
| 5,759,188 A | 6/1998 | Yoon |
| 5,772,672 A | 6/1998 | Toy et al. |
| 5,792,152 A | 8/1998 | Klein et al. |
| 5,797,927 A | 8/1998 | Yoon |
| 5,800,447 A | 9/1998 | Wenstrom, Jr. |
| 5,810,848 A | 9/1998 | Hayhurst |
| 5,810,852 A | 9/1998 | Greenberg et al. |
| 5,814,052 A | 9/1998 | Nakao et al. |
| 5,814,054 A | 9/1998 | Kortenbach |
| 5,814,069 A | 9/1998 | Schulze et al. |
| 5,817,107 A | 10/1998 | Schaller |
| 5,817,111 A | 10/1998 | Riza |
| 5,826,776 A | 10/1998 | Schulze et al. |
| 5,827,298 A | 10/1998 | Hart |
| 5,827,299 A | 10/1998 | Thomason et al. |
| 5,830,220 A | 11/1998 | Wan |
| 5,833,697 A | 11/1998 | Ludwick |
| 5,843,084 A | 12/1998 | Hart |
| 5,843,099 A | 12/1998 | Nichols et al. |
| 5,843,100 A | 12/1998 | Meade |
| 5,846,254 A | 12/1998 | Schulze et al. |
| 5,855,311 A | 1/1999 | Hamblin et al. |
| 5,860,749 A | 1/1999 | Hirakawa |
| 5,860,983 A | 1/1999 | Wenstrom, Jr. |
| 5,860,992 A | 1/1999 | Daniel et al. |
| 5,865,835 A | 2/1999 | Lolagne |
| 5,871,488 A | 2/1999 | Tovey et al. |
| 5,871,490 A | 2/1999 | Schulze et al. |
| 5,876,412 A | 3/1999 | Piraka |
| 5,879,371 A | 3/1999 | Phipps |
| 5,893,878 A | 4/1999 | Pierce |
| 5,895,393 A | 4/1999 | Pagedas |
| 5,895,395 A | 4/1999 | Yeung |
| 5,897,563 A | 4/1999 | Yoon |
| 5,897,564 A | 4/1999 | Qureshi |
| 5,897,574 A | 4/1999 | Bonutti |
| 5,899,911 A | 5/1999 | Carter |
| 5,904,692 A | 5/1999 | Steckel |
| 5,908,426 A | 6/1999 | Pierce |
| 5,908,428 A | 6/1999 | Scirica |
| 5,910,148 A | 6/1999 | Reimels et al. |
| 5,918,604 A | 7/1999 | Whelan |
| 5,919,199 A | 7/1999 | Mers Kelly et al. |
| 5,925,064 A | 7/1999 | Meyers et al. |
| 5,928,252 A | 7/1999 | Steadman |
| 5,931,844 A | 8/1999 | Thompson |
| 5,935,149 A | 8/1999 | Ek |
| 5,938,668 A | 8/1999 | Scirica |
| 5,941,439 A | 8/1999 | Seritella |
| 5,944,724 A | 8/1999 | Lizardi |
| 5,947,982 A | 9/1999 | Duran |
| 5,951,559 A | 9/1999 | Burkhart |
| 5,951,587 A | 9/1999 | Qureshi et al. |
| 5,954,733 A | 9/1999 | Yoon |
| 5,957,937 A | 9/1999 | Yoon |
| 5,964,773 A | 10/1999 | Greenstein |
| 5,968,047 A | 10/1999 | Reed |
| 5,980,538 A | 11/1999 | Fuchs |
| 5,980,557 A | 11/1999 | Iserin |
| 5,984,932 A | 11/1999 | Yoon |
| 5,993,451 A | 11/1999 | Burkhart |
| 5,993,466 A | 11/1999 | Yoon |
| 5,993,467 A | 11/1999 | Yoon |
| 6,004,332 A | 12/1999 | Yoon |
| 6,010,513 A | 1/2000 | Karhi |
| 6,017,358 A | 1/2000 | Yoon |
| 6,024,747 A | 2/2000 | Kontos |
| 6,045,561 A | 4/2000 | Skiba |
| 6,051,006 A | 4/2000 | Shluzas |
| 6,071,289 A | 6/2000 | Burbank, III |
| 6,074,403 A | 6/2000 | Nord |
| 6,077,276 A | 6/2000 | Kontos |
| 6,080,180 A | 6/2000 | Yoon |
| 6,086,601 A | 7/2000 | Yoon |
| 6,096,060 A | 8/2000 | Trott |
| 6,099,538 A | 8/2000 | Oren |
| 6,102,920 A | 8/2000 | Sullivan |
| 6,117,114 A | 9/2000 | Noble et al. |
| 6,117,144 A | 9/2000 | Nobles |
| 6,126,665 A | 10/2000 | Yoon |
| 6,132,433 A | 10/2000 | Whelan |
| 6,143,004 A | 11/2000 | Davis et al. |
| 6,143,005 A | 11/2000 | Yoon |
| 6,146,387 A | 11/2000 | Trott |
| 6,146,391 A | 11/2000 | Cigaina |
| 6,159,224 A | 12/2000 | Yoon |
| 6,183,485 B1 | 2/2001 | Thomason et al. |
| 6,197,035 B1 | 3/2001 | Loubens et al. |
| 6,200,329 B1 | 3/2001 | Fung et al. |
| 6,254,620 B1 | 7/2001 | Koh et al. |
| 6,322,570 B1 | 11/2001 | Matsutani |
| 6,332,889 B1 | 12/2001 | Sancoff |
| 6,383,199 B2 | 5/2002 | Carter |
| 6,454,777 B1 | 9/2002 | Green |
| 6,466,136 B2 | 10/2002 | Seguin |
| 6,475,135 B1 | 11/2002 | Levy |
| 6,485,504 B1 | 11/2002 | Johnson et al. |
| 6,500,184 B1 | 12/2002 | Chan |
| 6,511,487 B1 | 1/2003 | Oren et al. |
| 6,517,552 B1 | 2/2003 | Nord et al. |
| 6,533,795 B1 | 3/2003 | Tran et al. |
| 6,551,330 B1 | 4/2003 | Bain |
| 6,595,911 B2 | 7/2003 | Lovuolo |
| 6,599,298 B1 | 7/2003 | Forster et al. |
| 6,599,309 B1 | 7/2003 | Gilman |
| 6,605,096 B1 | 8/2003 | Ritchart |
| 6,616,694 B1 | 9/2003 | Schmieding |
| 6,623,492 B1 | 9/2003 | Berube et al. |
| 6,638,283 B2 | 10/2003 | Thal |
| 6,679,895 B1 | 1/2004 | Sancoff et al. |
| 6,719,764 B1 | 4/2004 | Gellman |
| 6,723,107 B1 | 4/2004 | Skiba |
| 6,743,241 B2 | 6/2004 | Kerr |
| 6,770,084 B1 | 8/2004 | Bain |
| 6,843,796 B2 | 1/2005 | Harari |
| 6,896,686 B2 | 5/2005 | Weber et al. |
| 6,984,237 B2 | 1/2006 | Hatch et al. |

(56) References Cited

U.S. PATENT DOCUMENTS

| | | |
|---|---|---|
| D523,554 S | 6/2006 | Weisel |
| D529,173 S | 9/2006 | Weisel |
| D530,421 S | 10/2006 | Topper et al. |
| 7,585,305 B2 | 9/2009 | Dreyfuss |
| 8,556,916 B2 | 10/2013 | Torrie |
| 8,591,527 B2 | 11/2013 | Fan et al. |
| 8,870,897 B2 | 10/2014 | Torrie |
| 9,456,818 B2 | 10/2016 | Torrie |
| 2002/0055758 A1 | 5/2002 | Sasaki |
| 2002/0065526 A1 | 5/2002 | Oren et al. |
| 2002/0103493 A1 | 8/2002 | Thal |
| 2002/0103494 A1 | 8/2002 | Pacey |
| 2002/0111534 A1 | 8/2002 | Suzuki et al. |
| 2002/0126845 A1 | 9/2002 | Hue |
| 2002/0128666 A1 | 9/2002 | Sancoff |
| 2002/0138084 A1 | 9/2002 | Weber |
| 2002/0147456 A1 | 10/2002 | Diduch et al. |
| 2002/0156344 A1 | 10/2002 | Pasricha et al. |
| 2002/0173800 A1 | 11/2002 | Dreyfuss |
| 2002/0193811 A1 | 12/2002 | Chan |
| 2003/0009186 A1 | 1/2003 | Mastri et al. |
| 2003/0023250 A1 | 1/2003 | Watschke et al. |
| 2003/0065337 A1 | 4/2003 | Topper et al. |
| 2003/0078585 A1 | 4/2003 | Johnson et al. |
| 2003/0078599 A1 | 4/2003 | O'Quinn et al. |
| 2003/0078600 A1 | 4/2003 | O'Quinn et al. |
| 2003/0083695 A1 | 5/2003 | Morris et al. |
| 2003/0105474 A1 | 6/2003 | Bonutti |
| 2003/0144674 A1 | 7/2003 | Loubens et al. |
| 2003/0176874 A1 | 9/2003 | Sauer |
| 2003/0216756 A1 | 11/2003 | Klein et al. |
| 2003/0233106 A1 | 12/2003 | Dreyfuss |
| 2003/0233108 A1 | 12/2003 | Gellman |
| 2004/0010273 A1 | 1/2004 | Diduch et al. |
| 2004/0073254 A1 | 4/2004 | Wyman |
| 2004/0127915 A1 | 7/2004 | Fleenor et al. |
| 2004/0193185 A1 | 9/2004 | McBrayer |
| 2004/0199184 A1 | 10/2004 | Topper et al. |
| 2004/0249393 A1 | 12/2004 | Weisel et al. |
| 2004/0249394 A1 | 12/2004 | Morris |
| 2004/0260314 A1 | 12/2004 | Lizardi |
| 2005/0021052 A1 | 1/2005 | Kim |
| 2005/0043748 A1 | 2/2005 | Oren et al. |
| 2005/0240219 A1 | 10/2005 | Kahle et al. |
| 2005/0251178 A1 | 11/2005 | Tirabassi et al. |
| 2006/0036265 A1 | 2/2006 | Dant |
| 2006/0069399 A1 | 3/2006 | Weisel et al. |
| 2007/0010829 A1 | 1/2007 | Nobles |
| 2007/0016249 A1 | 1/2007 | Reznik |
| 2007/0038230 A1 | 2/2007 | Stone et al. |
| 2007/0118152 A1 | 5/2007 | Page |
| 2007/0156172 A1 | 7/2007 | Alvarado |
| 2008/0027468 A1 | 1/2008 | Fenton et al. |
| 2008/0114378 A1 | 5/2008 | Matsushita |
| 2008/0154286 A1 | 6/2008 | Abbott et al. |
| 2008/0234729 A1 | 9/2008 | Page |
| 2008/0255591 A1 | 10/2008 | Harada |
| 2009/0018554 A1 | 1/2009 | Thorne et al. |
| 2009/0062819 A1 | 3/2009 | Burkhart et al. |
| 2009/0069824 A1 | 3/2009 | Chu |
| 2009/0069845 A1 | 3/2009 | Frushell |
| 2009/0082787 A1 | 3/2009 | Pang |
| 2009/0082788 A1 | 3/2009 | Elmaraghy |
| 2009/0131956 A1 | 5/2009 | Dewey et al. |
| 2009/0131976 A1 | 5/2009 | Kowalski |
| 2009/0198274 A1 | 8/2009 | Frushell |
| 2010/0042117 A1 | 2/2010 | Kim et al. |
| 2010/0076440 A1 | 3/2010 | Pamichev |
| 2010/0198235 A1 | 8/2010 | Pierce et al. |
| 2010/0268241 A1 | 10/2010 | Flom |
| 2010/0312179 A1 | 12/2010 | Nikolchev et al. |
| 2011/0245850 A1 | 10/2011 | Van Der Burg et al. |
| 2012/0209300 A1 | 8/2012 | Torrie |
| 2013/0035699 A1 | 2/2013 | Heneveld et al. |
| 2013/0046336 A1 | 2/2013 | Blumenkranz |
| 2014/0039529 A1 | 2/2014 | Torrie |
| 2014/0188138 A1 | 7/2014 | Meisheimer |
| 2014/0207188 A1 | 7/2014 | Yearsley et al. |

FOREIGN PATENT DOCUMENTS

| | | |
|---|---|---|
| EP | 0315371 | 5/1989 |
| EP | 0903109 | 3/1990 |
| EP | 0535906 | 4/1993 |
| EP | 0574707 | 5/1993 |
| EP | 0684012 | 11/1995 |
| EP | 0717957 A1 | 6/1996 |
| EP | 0778004 A1 | 6/1997 |
| EP | 0861632 A1 | 9/1998 |
| EP | 1243221 | 9/2002 |
| EP | 1334697 | 8/2003 |
| EP | 2353516 A1 | 8/2011 |
| WO | 1989010096 | 11/1989 |
| WO | 1992012674 | 8/1992 |
| WO | 1994028801 | 12/1994 |
| WO | 1995002363 | 1/1995 |
| WO | 1995008958 | 4/1995 |
| WO | 1995013021 | 5/1995 |
| WO | 1995022932 | 8/1995 |
| WO | 1996009796 | 4/1996 |
| WO | 1996027331 | 9/1996 |
| WO | 1996039946 | 12/1996 |
| WO | 1996039948 | 12/1996 |
| WO | 1997041780 | 11/1997 |
| WO | 1997047246 | 12/1997 |
| WO | 1998014126 | 4/1998 |
| WO | 1998030151 | 7/1998 |
| WO | 1998030152 | 7/1998 |
| WO | 1998030153 | 7/1998 |
| WO | 1998043545 | 10/1998 |
| WO | 1999012480 | 3/1999 |
| WO | 1999047050 | 9/1999 |
| WO | 2000012013 | 8/2000 |
| WO | 2000051498 | 9/2000 |
| WO | 2001095809 | 12/2001 |
| WO | 2002004322 | 1/2002 |
| WO | 2002022026 | 3/2002 |
| WO | 2002043558 | 6/2002 |
| WO | 2003099136 A1 | 12/2003 |
| WO | 2009138103 A1 | 11/2009 |
| WO | 2010078609 A1 | 7/2010 |
| WO | 2011008607 A1 | 1/2011 |
| WO | 2013119592 A1 | 8/2013 |

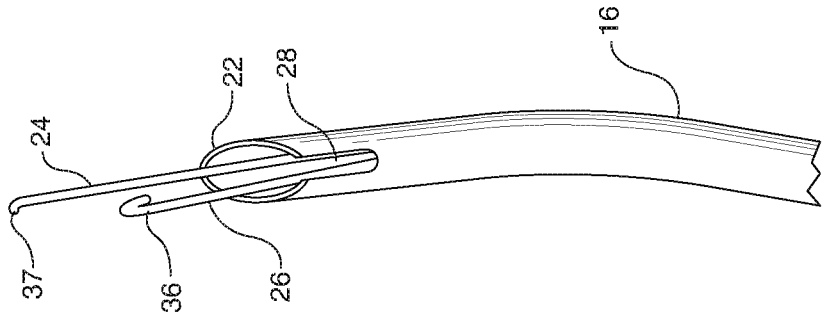
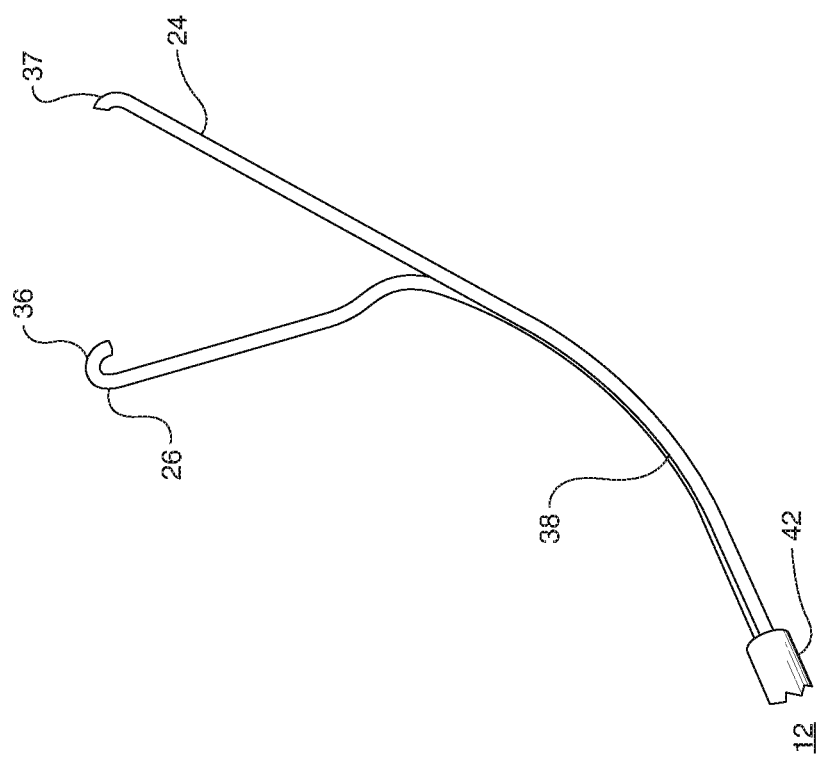

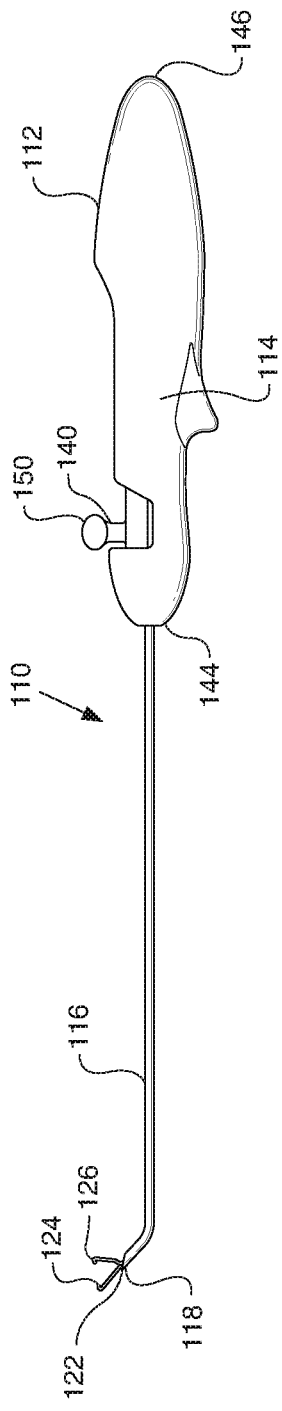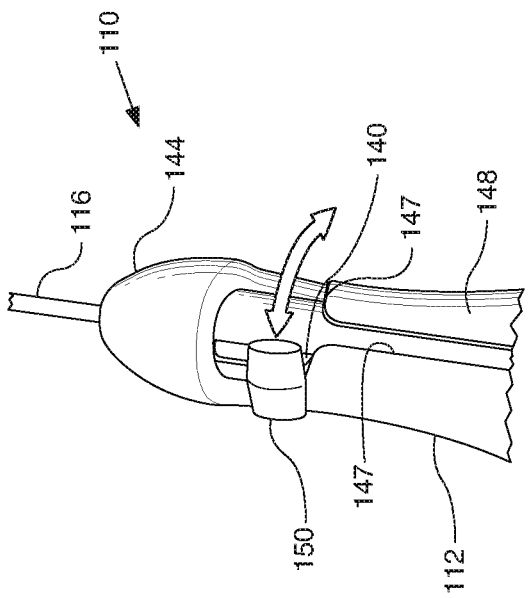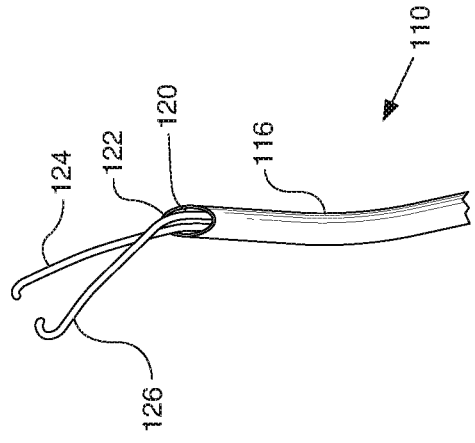

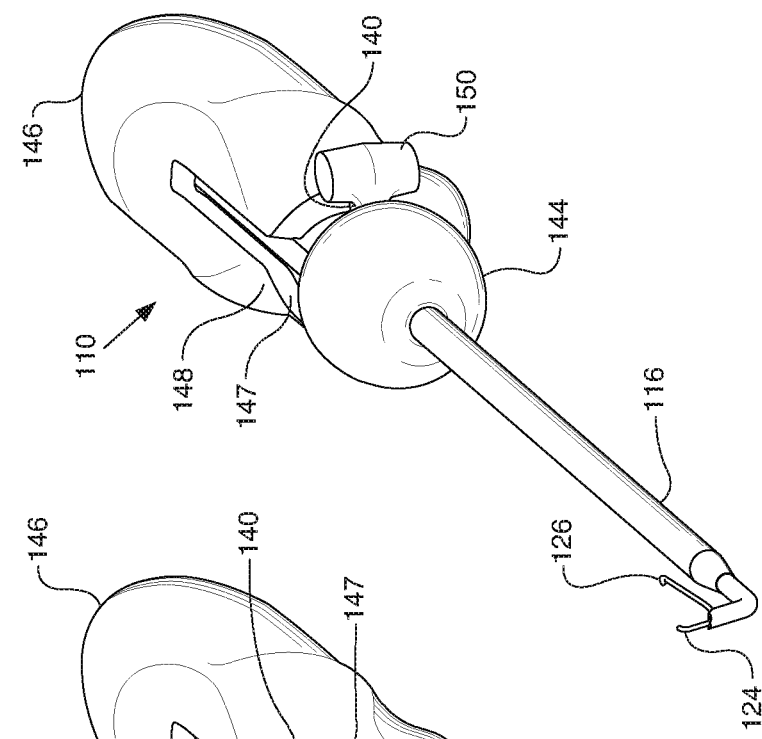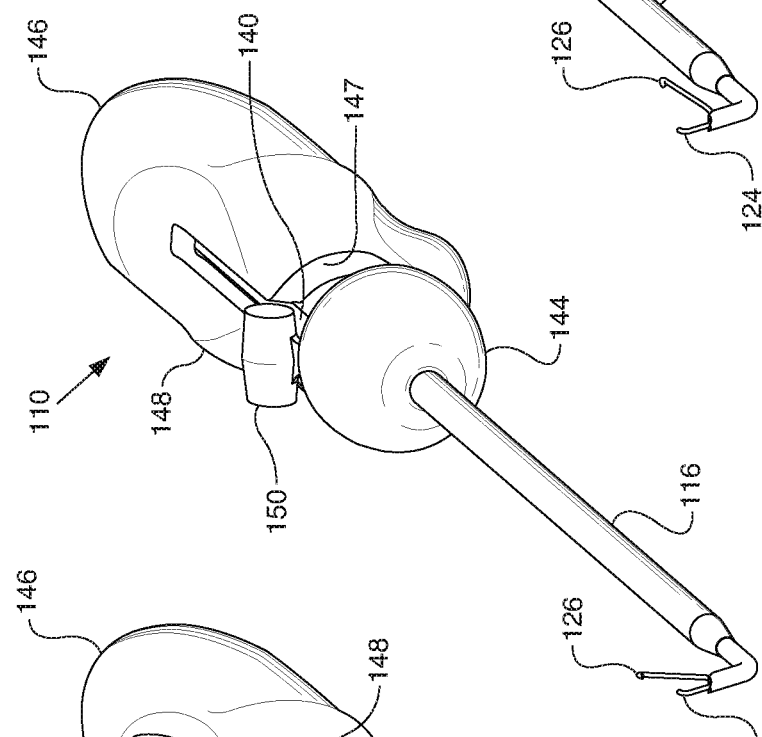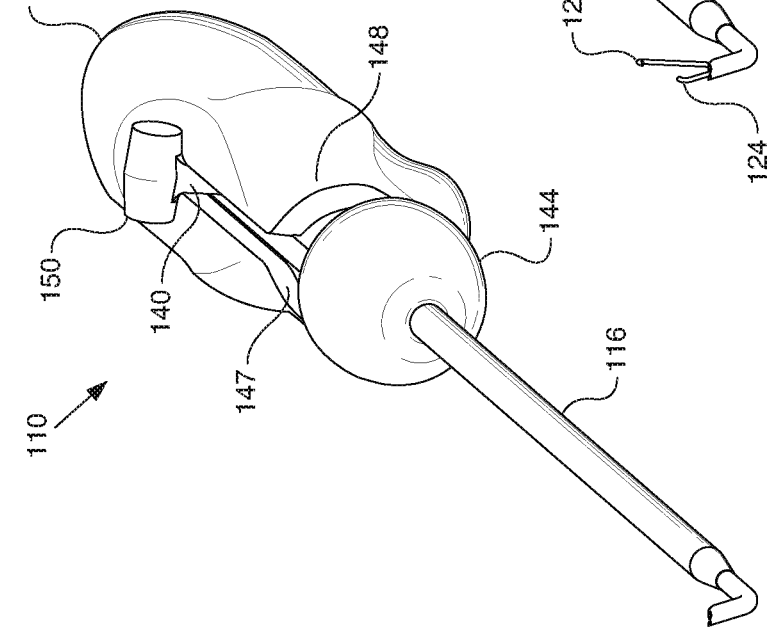

SUTURE PASSER AND GRASPER INSTRUMENT AND METHOD

CROSS-REFERENCE TO RELATED APPLICATIONS

This application claims benefit of U.S. Provisional Application No. 62/414,886, filed Oct. 31, 2016, the disclosure of which is incorporated herein by reference in its entirety.

FIELD

This disclosure relates to instruments for suturing tissues and, more particularly, to a device which passes or retrieves a suture within a patient and related methods.

BACKGROUND

Sutures are widely used within patients to secure two or more layers of soft tissue together, or to secure soft tissue to bone. During open surgical procedures, in which a large incision provides ready access to the tissues, surgeons have little difficulty in passing suture to the surgical site and then retrieving or withdrawing the suture to provide two free ends on either side of the tissue. The two ends of suture thereafter are knotted, or utilized for additional suturing of the tissue.

However, there are an increasing number of closed procedures in which access to tissues is provided through narrow passageways within one or more cannulas. During some endoscopic and arthroscopic procedures, a suture is delivered through a first cannula using an elongated needle and threaded through one side of the tissue. Thereafter, the suture must be retrieved through a second cannula using narrow grasper-type forceps or an elongated hollow suture retriever having an internal wire loop. The wire loop is extendable beyond the tip of the retriever to capture a free end of the suture. While graspers can grab a middle portion of a suture, the wire loop of the suture retriever can only be passed around a free end of the suture. Therefore, two or more instruments are typically required to perform endoscopic or arthroscopic suturing. Additional complexities arise when the suture length is inadequate to be easily captured by the suture grasper.

SUMMARY

Disclosed herein is a combination suture passer and grasper instrument having a needle which can deliver a suture to a repair site, and then use deformable wire arms to capture the suture and drag it into a hollow interior of the needle, thus eliminating the need for two separate instruments. Additionally, the sliding actuator of the instrument allows the wire arms and captured suture to be retracted further back into the needle as compared to a suture grasper using a plunger-type actuator. Advantageously, this allows a longer length of suture to be used during the repair procedure, thus making suture capture easier.

In examples, the suture passer and grasper instrument of this disclosure includes a hollow, elongate shaft having a proximal end, a distal end, and a longitudinal axis extending therebetween. The proximal end of the shaft is fixedly coupled to a handle, and the distal end of the shaft defines a tip for penetrating tissue. The instrument also includes an assembly disposed within the handle and the shaft, the assembly being axially moveable independent of the handle and the shaft. A distal end of the assembly is coupled to first and second wire-like members. At least one of the first and second wire-like members terminates in a hook-like element for grasping a suture. The handle also includes an actuator for causing the assembly to move the wire-like members from a retracted position, in which the wire-like members are proximal to the tip, to an extended position, in which the wire-like members are distal to the tip. In examples, a length of the first and second wire-like members is selected to be substantially the same.

In further examples of the instrument, the distal end of the shaft is curved upwardly so that a distal opening in the shaft faces laterally and the tip projects longitudinally. The distal opening of the shaft further defines a longitudinal slot extending proximally from the opening, the slot having a length and a width selected to allow passage of a suture. When the first and second wire-like members are in the extended position, the first and second wire-like members are linearly aligned between the tip and the slot. The first and second wire-like members are rotatable in both a clockwise and counterclockwise direction about a longitudinal axis extending between the first and second wire-like members. The first and second wire-like members are also rotatable in one or more full revolutions or a partial revolution about a longitudinal axis extending between the first and second wire-like members.

In yet further examples, a length of the instrument extending from a proximal end of the handle to the distal end of the shaft is between about 13 inches and about 14 inches. A length of the shaft extending from the handle is about 8 inches. One of the first and second wire-like members terminates in the hook-like element and the other of the first and second wire-like members terminates in a half-hook. The first and second wire-like members are made of a material having a circular cross-section. In examples, the actuator may be a thumb slide.

Examples of a method of manipulating a suture of this disclosure include: 1) piercing and extending a needle of a surgical instrument as described above through soft tissue; 2) extending the first and second wire-like members distally on either side of suture; 3) grasping the suture between the first and second wire-like members; and 4) retracting the wire-like members distally to a location at least partially within the distal end of the needle such that at least a portion of the suture is retained inside the needle.

In further examples, the method of this disclosure may include rotating the first and second wire-like members about an axis extending between the first and second wire-like members, wherein rotating the first and second wire-like members includes rotating the first and second wire-like members in either a clockwise or counter-clockwise direction and/or in one or more full revolutions or a partial revolution about a longitudinal axis extending between the first and second wire-like members. Piercing the needle of the surgical instrument through soft tissue includes piercing the tissue with the tip of the needle. Extending the first and second wire-like members distally on either side of suture includes moving an actuator slidably mounted to the handle from a first position, in which the actuator is closer to a proximal end of the handle, to a second position, in which the actuator is closer to a distal end of the handle. Grasping the suture between the first and second wire-like members includes grasping the suture with the hook-like element. Retracting the wire-like members distally includes moving an actuator slidably mounted to the handle from a second position, in which the actuator is closer to a distal end of the handle, to a first position, in which the actuator is closer to a proximal end of the handle.

Another embodiment of the invention includes a suture passer and grasper instrument. The instrument may include a hollow, elongate shaft having a proximal end, a distal end, and a longitudinal axis extending between the proximal end and the distal end, the proximal end of the shaft coupled to a handle, and the distal end of the shaft defining a tip configured to penetrate tissue, and an assembly disposed in part within the handle and in part within the hollow, elongate shaft, the assembly being axially and rotationally moveable independent of the handle and the hollow, elongate shaft. The assembly may include an actuator accessible near the handle; a connector coupled to the actuator; first and second wire-like members coupled to the connector, at least one of the first and second wire-like members capable of engaging a suture. Movement of the actuator is capable of moving the first and second wire-like members from a retracted position, in which the wire-like members are proximal to the tip of the distal end, to an extended position, in which the wire-like members are distal to the tip of the distal end, and capable of rotating at least one of the first and second wire-like members relative to the hollow, elongate shaft.

Yet another embodiment of the invention is a method of manipulating a suture. The method may include piercing and extending a surgical instrument into soft tissue, the surgical instrument including at least a hollow, elongate shaft having a proximal end, a distal end, and a longitudinal axis extending between the proximal end and the distal end, the proximal end of the shaft coupled to a handle, and the distal end of the shaft defining a tip configured to penetrate tissue; and an assembly disposed in part within the handle and in part within the hollow, elongate shaft, the assembly being axially and rotationally moveable independent of the handle and the hollow, elongate shaft. The assembly may include an actuator accessible near the handle; a connector coupled to the actuator; first and second wire-like members coupled to the connector, at least one of the first and second wire-like members terminating in a hook-like element capable of engaging a suture. The method may also include rotating one or both of the first and second wire-like members about an axis extending between the first and second wire-like members relative to the hollow, elongate shaft; moving the first and second wire-like members on either side of a suture; grasping the suture between the first and second wire-like members; and retracting the wire-like members proximally to a location at least partially within the distal end of the hollow, elongate shaft such that at least a portion of the suture is retained inside the hollow, elongate shaft.

Still another embodiment of the invention is a method of manipulating a suture. The method may include piercing and extending a surgical instrument into soft tissue. The surgical instrument includes at least a hollow, elongate shaft having a proximal end, a distal end, and a longitudinal axis extending between the proximal end and the distal end, the proximal end of the shaft coupled to a handle, and the distal end of the shaft defining a tip configured to penetrate tissue; and an assembly disposed in part within the handle and in part within the hollow, elongate shaft, the assembly being axially and rotationally moveable independent of the handle and the hollow, elongate shaft. The assembly may include an actuator accessible near the handle; a connector coupled to the actuator; first and second wire-like members coupled to the connector, at least one of the first and second wire-like members terminating in a hook-like element capable of engaging a suture. The method may further include extending the first and second wire-like members on either side of a suture by rotating the assembly relative to the handle and; grasping the suture between the first and second wire-like members by moving the actuator proximally relative to the handle; and retracting the wire-like members proximally to a location at least partially within the distal end of the hollow, elongate shaft such that at least a portion of the suture is retained inside the hollow, elongate shaft by moving the actuator proximally relative to the handle.

Further areas of applicability of the present disclosure will become apparent from the detailed description provided hereinafter. It should be understood that the detailed description and specific examples, while indicating the preferred example of the disclosure, are intended for purposes of illustration only and are not intended to limit the scope of the disclosure.

BRIEF DESCRIPTION OF THE DRAWINGS

The accompanying drawings, which are incorporated in and form a part of the specification, illustrate the examples of the present disclosure and together with the written description serve to explain the principles, characteristics, and features of the disclosure. In the drawings:

FIGS. 3A-3B are detailed views of the wire-like arms of the instrument of FIG. 1 in an extended position;

FIG. 6 illustrates an alternative embodiment of a suture passer and grasper instrument including rotatable arms;

FIGS. 7A-7B depict portions of the instrument shown in FIG. 6 in more detail with the instrument in an actuator rotational state;

FIG. 9 is a perspective view of the instrument of FIG. 6 illustrating an operative state of the instrument;

FIG. 10 is a perspective view of the instrument of FIG. 6 illustrating another operative state of the instrument; and FIG. 11 is a perspective view of the instrument of FIG. 6 illustrating still another operative state of the instrument.

DETAILED DESCRIPTION

The following description of the preferred example(s) is merely exemplary in nature and is in no way intended to limit the disclosure, its application, or uses.

To illustrate example(s) in a clear and concise manner, the drawings may not necessarily be to scale and certain features may be shown in somewhat schematic form. Features that are described and/or illustrated with respect to one example may be used in the same way or in a similar way in one or more other examples and/or in combination with or instead of the features of the other examples.

Comprise, include, and/or plural forms of each are open ended and include the listed parts and can include additional parts that are not listed. And/or is open ended and includes one or more of the listed parts and combinations of the listed parts.

Figure 1:
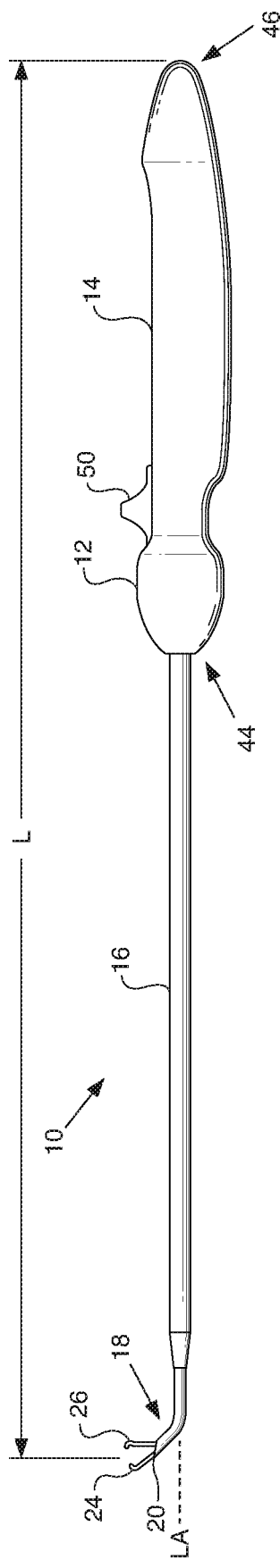
FIG. 1 is an illustration of an exemplary suture passer and grasper instrument of this disclosure.

Turning now to FIG. 1, an exemplary suture passer and grasper instrument 10 is illustrated. In FIG. 1, the instrument 10 generally includes a handle 12 including a grip portion 14, and an elongated, cannulated needle 16 which terminates in a distal end 18. An overall length L of the instrument 10 from the proximal end 46 of the handle 12 to the distal end 18 of the needle 16 is selected based on the type of repair procedure to be performed. For example, for a hip surgery, which requires a longer instrument than a knee or shoulder surgery, the overall length L of the instrument 10 may be about 13 to about 14 inches, which includes approximately 8.0 inches of the needle 16 extending from the distal end 44 of the handle 12. The needle 16 may be comprised of stainless steel hypodermic tubing, although other suitable materials are contemplated by this disclosure. The needle 16 terminates with a distal opening 20 in communication with an interior of the needle 16, as further described below. In the example shown, the handle 12 is formed in an in-line configuration, substantially co-axial with a longitudinal axis LA of the needle 16. In alternative examples, not shown, the handle 12 may be formed in a pistol-grip or other suitable configuration. The grip portion 14 of the handle 12 is configured to be held and manipulated by a user.

Still referring to FIG. 1, a pair of retractable, deformable wire-like arms 24, 26 for manipulating suture project from the distal opening 20 of the needle 16 in an extended position, as further described below. The wire-like arms 24, 26 may be formed of stainless steel music wire or other suitable materials having a cylindrical cross-section. The wire-like arms 24, 26 may be made of the same material or of a different material having a different tensile strength and/or degree of flexibility. In the extended position, the wire-like arms 24, 26 are naturally sprung apart, but when they are retracted into the needle 16, they are forced together. Similarly, when the wire-like arms 24, 26 are extended from the distal opening 20 of the needle 16, they resume their biased state, which is apart. Thus, a distal/proximal motion of the wire-like arms 24, 26 relative to the needle 16 creates an opening/closing motion of the wire-like arms 24, 26, which can be used for suture manipulation, as further described below.

Figure 2:
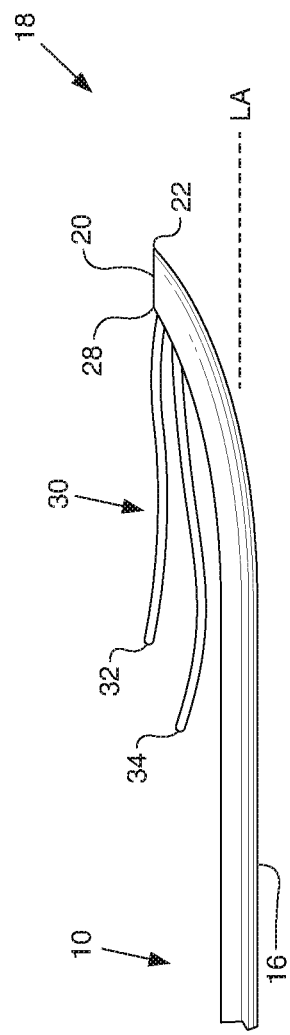
FIG. 2 is a detail of the distal end of the needle of FIG. 1.

As shown in FIG. 2, the distal end 18 of the needle 16 may be curved or bent upwardly such that distal opening 20 faces laterally, while a sharp tip 22 for penetrating tissue projects longitudinally relative to the longitudinal axis LA of the needle 16. The needle 16 further includes a longitudinal suture slot 28 which terminates at its distal end with the distal opening 20. A length and width of the slot 28 is selected to accommodate the passage of one or more sutures, with radiused edges to avoid damage to suture. As illustrated in FIG. 2, a portion of a suture 30 is carriable by the instrument 10 when the wire-like arms 24, 26 (FIGS. 1, 3A, 3B, and 5A-5C) are in a retracted position, such that suture legs 32, 34 extend from the slot 28. This configuration is particularly useful for passing the suture 30 through tissue using the tip 22, as described in more detail below.

Turning now to FIG. 3A, each of the wire-like arms 24, 26 terminates in a common linking member 38. The linking member 38 may be curved to accommodate the curvature at the distal end 18 of the needle 16. The linking member 38 is secured to a rod 42 or other element disposed within the handle 12, as further described below. In other examples, not shown, the wire-like arms 24, 26 may be formed from a single, U-shaped wire whose central portion is secured to the rod 42. A length of one of the wire-like arms 24, 26 may be the same as or longer/shorter than the length of the other of the wire-like arms 24, 26. Substantially equal length wire-like arms 24, 26 may avoid the suture from being captured by one arm 24, 26 only. Additionally, if both wire-like arms 24, 26 are substantially equal in length, the user knows at the beginning of the retraction stroke whether the suture is within reach. At least one of the wire-like arms 24, 26 (preferably the stronger/more rigid arm where present) terminates in a full hook 36 to aid in grasping suture. The other of the wire-like arms 24, 26 may terminate in a partial hook 37 (FIG. 3A), another full hook 36 (FIGS. 5A-5C), or may be straight-sided. As shown in FIG. 3B, when the wire-like arms 24, 26 are in the extended position, they are substantially linearly aligned between the tip 22 and the suture slot 28 of the needle 16 such that the hooks 36, 37 are curved in toward each other.

Figure 4:
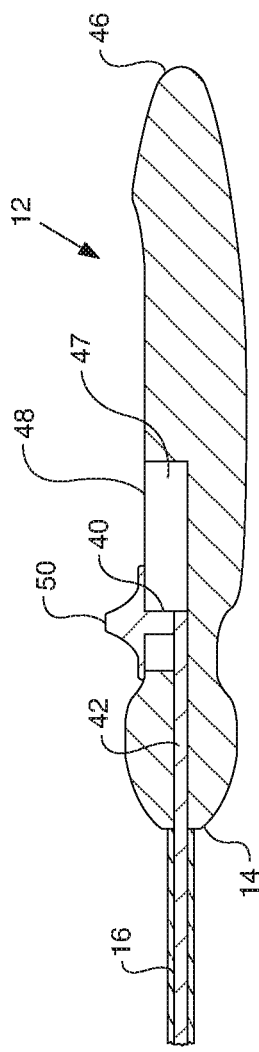
FIG. 4 is a cross-section of an exemplary handle of the instrument of FIG. 1 including an actuator.

FIG. 4 illustrates a cross-section of an exemplary handle 12 of this disclosure. In FIG. 4, the handle 12 includes an actuator 50 (e.g. a thumb slide) slidably mounted to a sidewall 48 of the handle 12. In the example of FIG. 4, the actuator 50 has a linear base and angled sides to be easily manipulated in either of two directions by a user's thumb. However, other suitable configurations of the actuator 50 are contemplated by this disclosure. The actuator 50 is mounted to the handle 12 so as to slide in a direction substantially parallel to the longitudinal axis LA of the needle 16. Specifically, the actuator 50 is moveable from a first position, in which the actuator 50 is closest to the proximal end 46 of the handle 12, to a second position, in which the actuator 50 is closest to the distal end 44 of the handle 12. The actuator 50 may also be selectively positioned at locations between the first and second positions, as described in more detail below.

Still referring to FIG. 4, the actuator 50 communicates with the interior of the handle 12 through a transverse member 40. The transverse member 40 may extend through a slot 47 in the sidewall 48 of the handle 12 along which the actuator 50 slides. The transverse member 40 in turn is connected to the elongated rod 42 of FIG. 3A. In various embodiments, the rod 42 may be solid or a hollow tube formed of stainless steel or other suitable materials. The rod 42 extends from the transverse member 40 in the interior of the handle 12 to the interior of the needle 16 so as to communicate with the wire-like arms 24, 26 (FIGS. 1, 3A, 3B, and 5A-5C). Thus, movement of actuator 50 relative to the handle 12 causes movement of the wire-like arms 24, 26 relative to the needle 16. Specifically, movement of the actuator 50 distally causes the rod 42 to move distally, thereby causing the wire-like arms 24, 26 to extend from the needle 16. In similar fashion, movement of the actuator 50 proximally causes the reverse motion of the rod 42.

In alternative examples, not shown, the position of the rod 42 is fixed relative to the handle 12, while the needle 16 is mechanically engaged to the actuator 50 and axially movable with respect to the rod 42. In this example, the needle 16 may be actuated by a user to slide over the wire-like arms 24, 26 proximally or distally to create the extended and retracted positions of the wire-like arms 24, 26.

In additional examples, not shown, the handle 12 may include a locking mechanism in mechanical communication with the rod 42 that inhibits motion of the rod 42 and the actuator 50 with respect to the needle 16. The locking mechanism may be one or more mechanical stops that fix the position of the rod 42 with respect to the needle 16 at one or more selected locations (e.g., the retracted position, the extended position, and intermediate positions there-between). In other examples, a locking mechanism that inhibits motion of the rod 42 with respect to the needle 16 may be omitted from the instrument 10 and the rod 42 may be free to axially slide to any location within and including the extended and retracted positions.

Figure 5C:
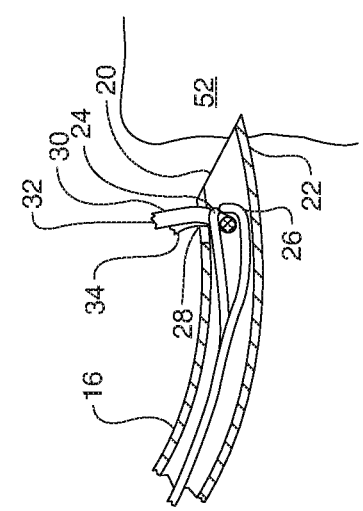
FIGS. 5A-5C show a method of retrieving suture through tissue using the instrument of FIG. 1.
Figure 5B:
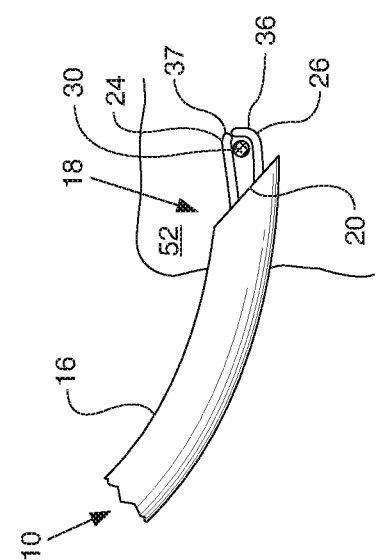
Figure 5A:
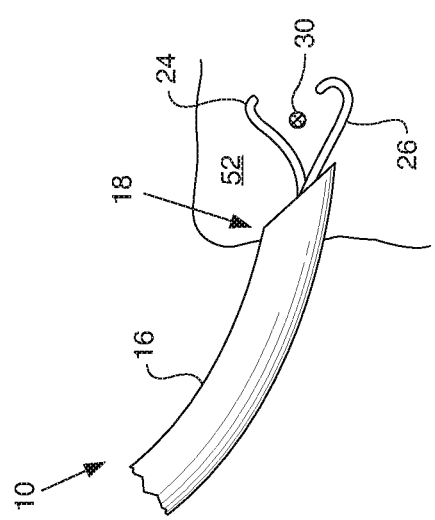

Extended, intermediate and retracted positions of the wire-like arms 24, 26 of the instrument 10 are further illustrated in FIGS. 5A-5C in use during a surgical procedure. In FIG. 5A, the needle 16 is shown with its distal end 18 piercing and extending through soft tissue 52. The wire-like arms 24, 26 are shown in an extended position passing on either side of a surgical suture 30. During suture retrieval, as shown in FIG. 5B, the wire-like arms 24, 26 are drawn proximally at least partially within the distal end 18 of the needle 16. As discussed above, a camming effect against the rim of the opening 20 forces the wire-like arms 24, 26 toward each other to encircle the suture 30 using the full hooks 36.

At this point, a user may choose to withdraw the instrument 10 from the tissue 52 while the wire-like arms 24, 26 are in the intermediate position to enable relative movement between the suture 30 and the wire-like arms 24, 26. This is especially useful when it is desired to access one end of the suture 30 while leaving the remainder of the suture 30 on the far side of the tissue 52. Alternatively, the wire-like arms 24, 26 may be further drawn into a retracted position (further proximal movement relative to the needle 16) while the needle 16 is piercing the tissue 52. Relative movement between the suture 30 and the instrument 10 is thereby inhibited, and the instrument 10 may thereafter be withdrawn from the tissue 52, as shown in FIG. 5C.

As discussed above with regard to FIG. 2, the suture slot 28 in the distal end 18 of the needle 16 enables the legs 32, 34 of the suture 30 to easily follow behind the tip 22 of the needle 16 while overall still presenting a low profile of the needle 16. Furthermore, while disposed within the slot 28, the suture 30 avoids contact damage which might otherwise occur with sharp edges surrounding the distal opening 20 of the needle 16, or by abrasion against tissue or other instruments. The tissue penetration ability of distal end 18 of the needle 16 also remains unencumbered by the suture 30 when it rests in the slot 28.

An alternative example of a suture passer and grasper instrument 110 is shown in FIGS. 6-11. The instrument 110 generally includes a handle 112 including a grip portion 114, and an elongated, cannulated shaft 116 (also referred to as a needle) which terminates in a distal end 118. An overall length of the instrument 110 from the proximal end 146 of the handle 112 to the distal end 118 of the hollow, elongate shaft 116 is selected based on the type of repair procedure to be performed. For example, for a hip surgery, which requires a longer instrument than a knee or shoulder surgery, the overall length of the instrument 110 may be about 13 to about 14 inches, which includes approximately 8.0 inches of the hollow, elongate shaft 116 extending from the distal end 144 of the handle 112. The hollow, elongate shaft 116 may be comprised of stainless steel hypodermic tubing, although other suitable materials are contemplated by this disclosure. The hollow, elongate shaft 116 terminates with a distal opening 120 (FIG. 7A) in communication with an interior of the hollow, elongate shaft 116, as further described below. In the example shown, the handle 112 is formed in an in-line configuration, substantially co-axial with a longitudinal axis of the hollow, elongate shaft 116. In alternative examples, not shown, the handle 112 may be formed in a pistol-grip or other suitable configuration. The grip portion 114 of the handle 12 is configured to be held and manipulated by a user.

Figure 8:
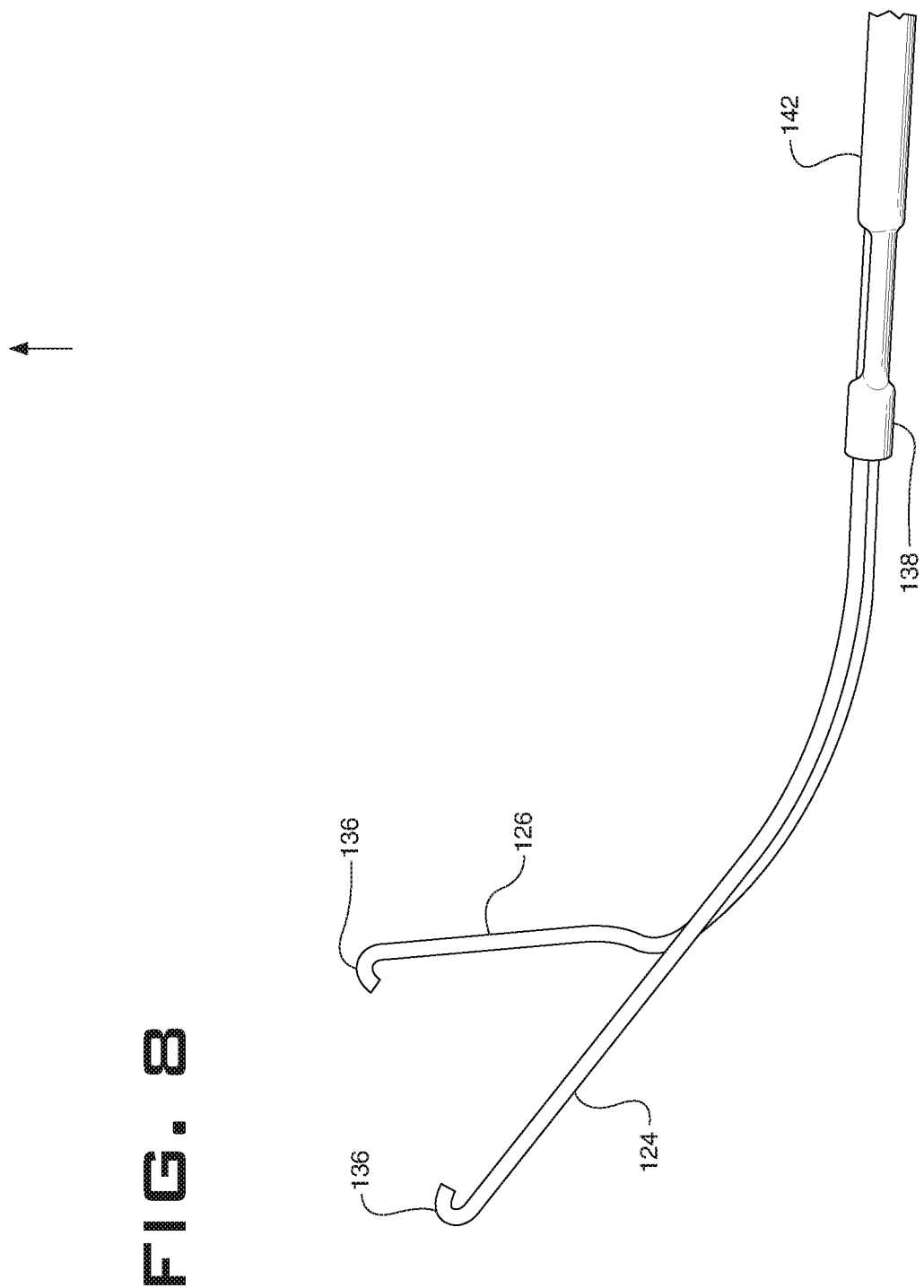
FIG. 8 is an elevation view a portion of the inner assembly of the instrument of FIG. 6.

A distal end of the instrument 110 is shown in more detail in FIG. 7A with rotatable wire-like arms 124, 126. In this type of implementation, the wire-like arms 124, 126 may be joined together proximal of their distal ends by twisting, by side-by-side fixation to one another or to another component, or by any other effective mechanism to establish a coupling, such as a linking member 138 as shown in FIG. 8. One or both of the wire-like arms 124, 126 may be rotatable in both a clockwise and counterclockwise direction about a longitudinal axis extending between the wire-like arms 124, 126 by rotation of the linking member 138 within a cannulated hollow, elongate shaft 116. Rotation of the linking member 138 in the illustrated embodiment is accomplished by rotation of a rod 142 (FIG. 8) connected to an actuator 150 that is disposed within and rotatable relative to a handle 112, as indicated by the action arrow in FIG. 7B. One or both of the wire-like arms 124, 126 may be rotatable in one or more full revolutions or a partial revolution, which may be about 45 degrees. Use of the instrument 110 is advantageous in cases where it is desirable to alter the orientation of the wire-like arms 124, 126 to increase the grasping area without rotation of the entire instrument 110. In the illustrated embodiment, the actuator 150 of the handle 112 is adapted to be rotationally (circumferentially) as well as axially moveable about the handle 112 for rotating the linking member 138, as will be further described in association with FIGS. 9-11. In other embodiments, an actuator for rotating the wire-like arms 124, 126 may be a separate component from a translational actuator.

The wire-like arms 124, 126 may be made of the same material or of a different material having a different tensile strength and/or degree of flexibility. In the extended position, the wire-like arms 124, 126 are naturally sprung apart, but when the wire-like arms 124, 126 are retracted into the hollow, elongate shaft 116, they are forced together. Similarly, when the wire-like arms 124, 126 are extended from the distal opening 120 of the hollow, elongate shaft 116, they resume their biased state, which is apart. Thus, a distal/proximal motion of the wire-like arms 124, 126 relative to the hollow, elongate shaft 116 creates an opening/closing motion of the wire-like arms 124, 126, which can be used for suture manipulation.

The distal end 118 of the hollow, elongate shaft 116 may be curved or bent such that distal opening 120 (FIG. 7A) faces laterally, while a sharp tip 122 (FIGS. 6-7A) for penetrating tissue projects longitudinally relative to the longitudinal axis of the hollow, elongate shaft 116. Some embodiments of a hollow, elongate shaft may further include a longitudinal suture slot which terminates at its distal end with the distal opening, similar to the slot 28 described above. A length and width of such a slot is selected to accommodate the passage of one or more sutures, with radiused edges to avoid damage to suture.

As shown in FIG. 8, each of the wire-like arms 124, 126 terminates in the common linking member 138. The linking member 138 may be curved to accommodate the curvature at the distal end 118 of the hollow, elongate shaft 116. The linking member 138 illustrated is secured to the rod 142. In other examples, not shown, the wire-like arms may be formed from a single, U-shaped wire whose central portion is secured to a rod or other member. A length of one of the wire-like arms may be the same as or longer/shorter than the length of the other of the wire-like arms. Substantially equal length wire-like arms 124, 126, as illustrated, may avoid the suture from being captured by one wire-like arm 124, 126 only. Additionally, if both wire-like arms 124, 126 are substantially equal in length, the user knows at the beginning of the retraction stroke whether the suture is within reach. At least one of the wire-like arms 124, 126 may terminate in a full hook 136 to aid in grasping suture. The other of the wire-like arms may terminate in a partial hook, as described in association with FIG. 3A above, or be configured in any other effective configuration.

As shown in FIGS. 7B and 9-11, the handle 112 interacts with the actuator 150 (e.g. a thumb slide) slidably and rotatably mounted with the handle 112. The actuator 150 is mounted to the handle 112 so as to slide in a direction substantially parallel to the longitudinal axis of the hollow, elongate shaft 116. Specifically, the actuator 150 is moveable from a first position, in which the actuator 150 is closest to the proximal end 146 of the handle 112 (FIG. 9), to a second position, in which the actuator 150 is closest to the distal end 144 of the handle 112 (FIG. 10). The actuator 150 may also be selectively positioned at locations between the first and second positions. As shown in FIG. 11, the actuator 150 may be rotated relative to the handle 112 to rotate one or both of the wire-like arms 124, 126 to enable grasping of a suture at other angles and at other distances relative to the hollow, elongate shaft 116.

The actuator 150 illustrated is coupled to the rod 142 through a transverse member 140 (FIGS. 6, 7B, and 9-11). The transverse member 140 may extend through a slot 147 in the sidewall 148 of the handle 112 along which the actuator 150 slides. The transverse member 140 in turn is connected to the elongated rod 142 of FIG. 8. In various embodiments, the rod 142 may be solid or a hollow tube formed of stainless steel or other suitable materials. The rod 142 extends from the transverse member 140 in the interior of the handle 112 to the interior of the hollow, elongate shaft 116 so as to communicate with the wire-like arms 124, 126. Thus, movement of actuator 150 relative to the handle 112 causes movement of the wire-like arms 124, 126 relative to the hollow, elongate shaft 116. Specifically, movement of the actuator 150 distally causes the rod 142 to move distally, thereby causing the wire-like arms 124, 126 to extend from the hollow, elongate shaft 116. In similar fashion, movement of the actuator 150 proximally causes the reverse motion of the rod 142.

In alternative examples, not shown, the position of a rod is fixed relative to a handle while a hollow, elongate shaft is mechanically engaged to an actuator and axially movable with respect to the rod. In this example, the hollow, elongate shaft may be actuated by a user to slide over the wire-like arms proximally or distally to create the extended and retracted positions of the wire-like arms.

In additional examples, not shown, the handle 112 may include a locking mechanism in mechanical communication with the rod 142 that inhibits motion of the rod 142 and the actuator 150 with respect to the hollow, elongate shaft 116. The locking mechanism may be one or more mechanical stops that fix the position of the rod 142 with respect to the hollow, elongate shaft 116 at one or more selected locations (e.g., the retracted position, the extended position, and intermediate positions there-between). In other examples, a locking mechanism that inhibits motion of the rod 142 with respect to the hollow, elongate shaft 116 may be omitted from the instrument 110 and the rod 142 may be free to axially slide to any location within and including the extended and retracted positions.

Surgical manipulations conducted with the instrument 110 are essentially similar to the manipulations described in association with the instrument 10 above and illustrated in FIGS. 5A-5C except that the instrument 110 is also capable of rotating one or both of the wire-like arms 124, 126 relative to the hollow, elongate shaft 116 to aid in aligning the instrument 110 to capture suture within the wire-like arms 124, 126.

Although specific features of the disclosure are shown in some drawings and not in others, this is for convenience only as each feature may be combined with any or all of the other features in accordance with the disclosure. Other examples will occur to those skilled in the art and are within the following claims.

What is claimed is:

1. A suture passer and grasper instrument comprising:
a hollow, elongate shaft having a proximal end, a distal end, and a longitudinal axis extending between the proximal end and the distal end, the proximal end of the shaft coupled to a handle, and the distal end of the shaft defining a tip configured to penetrate tissue, the handle includes a longitudinal slot having a perpendicular portion disposed at a distal end of the longitudinal slot; and
an assembly disposed in part within the handle and in part within the hollow, elongate shaft, the assembly being axially and rotationally moveable independent of the handle and the hollow, elongate shaft, the assembly comprising:
an actuator disposed within the longitudinal slot of the handle;
a connector coupled to the actuator;
first and second wire-like members coupled to the connector, at least one of the first and second wire-like members configured to engage a suture;
wherein movement of the actuator within the longitudinal slot is configured to move the first and second wire-like members from a retracted position, in which the wire-like members are proximal to the tip of the distal end, to an extended position, in which the wire-like members are distal to the tip of the distal end, and movement of the actuator within the perpendicular portion is configured to rotate at least one of the first and second wire-like members relative to the hollow, elongate shaft.

2. The instrument of claim 1, wherein the distal end of the hollow, elongate shaft is curved away from the longitudinal axis so that a distal opening in the hollow, elongate shaft faces at least in part laterally and the tip projects longitudinally.

3. The instrument of claim 2, wherein the distal opening of the hollow, elongate shaft includes a longitudinal slot extending proximally from the opening, the slot having a length and a width selected to allow passage of a suture.

4. The instrument of claim 3, wherein, when the first and second wire-like members are in the extended position, the first and second wire-like members are linearly aligned between the tip and the slot.

5. The instrument of claim 1, wherein the connector includes a rod coupled between the actuator and the first and second wire-like members.

6. The instrument of claim 5, wherein the connector includes a linking member coupled between the rod and the first and second wire-like members.

7. The instrument of claim 1, wherein the actuator is configured to rotate at least one of the first and second wire-like members relative to the hollow, elongate shaft in both a clockwise and a counterclockwise direction.

8. The instrument of claim 1, wherein the actuator is configured to rotate at least one of the first and second wire-like members relative to the hollow, elongate shaft in one or more full revolutions or a partial revolution.

9. The instrument of claim 1, wherein a length of the instrument extending from a proximal end of the handle to the tip is between about 13 inches and about 14 inches.

10. The instrument of claim 1, wherein a length of the hollow, elongate shaft extending from the handle is about 8 inches.

11. The instrument of claim 1, wherein at least one of the first and second wire-like members terminates in a hook-like element capable of engaging a suture.

12. The instrument of claim 1, wherein one of the first and second wire-like members terminates in the hook-like element and the other of the first and second wire-like members terminates in a half-hook.

13. The instrument of claim 1, wherein the first and second wire-like members are comprised of a material having a circular cross-section.

14. The instrument of claim 1, wherein a length of the first and second wire-like members is selected to be substantially the same.

15. The instrument of claim 1, wherein the actuator is a thumb slide.

16. A method of manipulating a suture comprising:
piercing and extending a surgical instrument into soft tissue, the surgical instrument comprising:
a hollow, elongate shaft having a proximal end, a distal end, and a longitudinal axis extending between the proximal end and the distal end, the proximal end of the shaft coupled to a handle, and the distal end of the shaft defining a tip configured to penetrate tissue, the handle includes a longitudinal slot having a perpendicular portion disposed at a distal end of the longitudinal slot; and
an assembly disposed in part within the handle and in part within the hollow, elongate shaft, the assembly being axially and rotationally moveable independent of the handle and the hollow, elongate shaft, the assembly comprising:
an actuator disposed within the longitudinal slot of the handle;
a connector coupled to the actuator;
first and second wire-like members coupled to the connector, at least one of the first and second wire-like members terminating in a hook-like element configured to engage a suture;
rotating one or both of the first and second wire-like members about an axis extending between the first and second wire-like members relative to the hollow, elongate shaft by moving the actuator along the perpendicular portion;
moving the first and second wire-like members on either side of a suture;
grasping the suture between the first and second wire-like members; and
retracting the wire-like members proximally to a location at least partially within the distal end of the hollow, elongate shaft such that at least a portion of the suture is retained inside the hollow, elongate shaft.

17. The method of claim 16, wherein piercing and extending the surgical instrument into soft tissue includes piercing the tissue with the tip of the hollow, elongate shaft.

18. The method of claim 16, wherein rotating one or both of the first and second wire-like members comprises rotating the actuator relative to the handle.

19. The method of claim 16, wherein rotating one or both of the first and second wire-like members comprises rotating the first and second wire-like members in either a clockwise or counter-clockwise direction.

20. The method of claim 16, wherein rotating one or both of the first and second wire-like members comprises rotating the first and second wire-like members in one or more full revolutions or a partial revolution about a longitudinal axis extending between the first and second wire-like members.

21. The method of claim 16, wherein moving the first and second wire-like members on either side of a suture comprises moving the actuator distally relative to the handle.

22. The method of claim 16, wherein rotating one or both of the first and second wire-like members about an axis extending between the first and second wire-like members relative to the hollow, elongate shaft includes rotating the actuator relative to the handle.

23. The method of claim 16, wherein grasping the suture between the first and second wire-like members comprises grasping the suture with the hook-like element.

24. The method of claim 16, wherein grasping the suture between the first and second wire-like members comprises moving the actuator proximally.

25. The method of claim 24, wherein retracting the wire-like members proximally comprises moving the actuator further proximally.

26. A method of manipulating a suture comprising:
piercing and extending a surgical instrument into soft tissue, the surgical instrument comprising:
a hollow, elongate shaft having a proximal end, a distal end, and a longitudinal axis extending between the proximal end and the distal end, the proximal end of the shaft coupled to a handle, and the distal end of the shaft defining a tip configured to penetrate tissue, the handle includes a longitudinal slot having a perpendicular portion disposed at a distal end of the longitudinal slot; and
an assembly disposed in part within the handle and in part within the hollow, elongate shaft, the assembly being axially and rotationally moveable independent of the handle and the hollow, elongate shaft, the assembly comprising:
an actuator disposed within the longitudinal slot of the handle;
a connector coupled to the actuator;
first and second wire-like members coupled to the connector, at least one of the first and second wire-like members terminating in a hook-like element configured to engage a suture;
extending the first and second wire-like members on either side of a suture by rotating the assembly relative to the handle and;
grasping the suture between the first and second wire-like members by moving the actuator proximally along the longitudinal slot; and
retracting the wire-like members proximally to a location at least partially within the distal end of the hollow, elongate shaft such that at least a portion of the suture is retained inside the hollow, elongate shaft by moving the actuator proximally relative to the handle.

27. The method of claim 26, wherein piercing and extending a surgical instrument into soft tissue comprises piercing the tissue with the tip of the hollow, elongate shaft.

28. The method of claim 26, wherein rotating the assembly comprises rotating the assembly in either a clockwise or counter-clockwise direction.

29. The method of claim 26, wherein rotating the assembly comprises rotating the assembly in one or more full revolutions or a partial revolution about a longitudinal axis extending between the first and second wire-like members.

30. The method of claim 26, wherein extending the first and second wire-like members on either side of suture by rotating the assembly relative to the handle also includes moving the actuator relative to the handle from a first position to a second position wherein the second position is more distal than the first position.

31. The method of claim 26, wherein grasping the suture between the first and second wire-like members comprises grasping the suture with the hook-like element.

\* \* \* \* \*